United States Patent
Kelly et al.

(10) Patent No.: US 6,187,820 B1
(45) Date of Patent: Feb. 13, 2001

(54) MEDICAL TREATMENT TO IMPROVE LIPID LEVELS

(75) Inventors: Peter Finian Kelly; Stephen Paul Jones, both of Nottingham (GB)

(73) Assignee: Knoll Aktiengesellschaft, Ludwigshafen (DE)

( * ) Notice: Under 35 U.S.C. 154(b), the term of this patent shall be extended for 0 days.

(21) Appl. No.: 09/269,340

(22) PCT Filed: Sep. 15, 1997

(86) PCT No.: PCT/EP97/05040

§ 371 Date: Mar. 25, 1999

§ 102(e) Date: Mar. 25, 1999

(87) PCT Pub. No.: WO98/13034

PCT Pub. Date: Apr. 2, 1998

(30) Foreign Application Priority Data

Sep. 25, 1996 (GB) .................................... 9619961

(51) Int. Cl.[7] .................................................. A61K 31/135
(52) U.S. Cl. ............................................ 514/646; 514/824
(58) Field of Search ...................................... 514/646, 824

(56) References Cited

FOREIGN PATENT DOCUMENTS

| 2098602 | 11/1982 | (GB) . |
| 90/06110 | 6/1990 | (WO) . |
| WO 95/20949 | * 8/1995 | (WO) . |

OTHER PUBLICATIONS

Lean, Mej, *Int. J. Obes. Relat. Metab. Disord.*, vol. 21, pp. S30–S36, 1997.
Weiser et al., *J. Clin. Pharmacol.*, vol. 36, No. 6, pp. 453–473, 1997.

* cited by examiner

*Primary Examiner*—Kimberly Jordan
(74) *Attorney, Agent, or Firm*—Keil & Weinkauf

(57) ABSTRACT

A compound of formula I

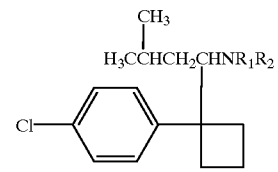

or a pharmaceutically acceptable salt thereof in which $R_1$ and $R_2$ are independently H or methyl (for example N,N-dimethyl-1-[1-(4-chlorophenyl)cyclobutyl]-3-methylbutyl amine hydrochloride optionally in the form of its monohydrate) is used for lowering lipid levels and/or increasing the HDL: LDL cholesterol ratio in humans, for example in humans having hyperlipidaemia, hypercholesterolaemia or hypertriglyceridaemia.

7 Claims, No Drawings

MEDICAL TREATMENT TO IMPROVE LIPID LEVELS

This application is a 371 of PCT/EP97/05040, filed Sep. 15, 1997.

This invention relates to a method of improving lipid levels in the human body.

Complications of atherosclerosis, such as myocardial infarction, stroke and peripheral vascular disease are a major cause of mortality and morbidity. In addition, the quality of life of millions of people is adversely affected by angina and heart failure caused by coronary heart disease. Hyperlipidaemia has been associated with an increased risk of developing these conditions. For this reason it is desirable to understand the etiology of hyperlipidaemia and to develop effective treatments for this condition. Hyperlipidaemia has been defined as plasma cholesterol and triglyceride levels that exceed "normal" (95th percentile of levels of the general population) levels. However, the ideal cholesterol level is much less than the normal level of the general population. Many people have cholesterol levels above the ideal (hypercholesterolaemia) and are therefore at an elevated risk of coronary artery disease (CAD). It is known that reducing the cholesterol level in such people is very effective in reducing the risk of CAD. Hypertriglyceridaemia may also be involved in atherosclerosis and can, in extreme cases, cause potentially life-threatening pancreatitis.

There are several ways in which treatment of people with high lipid levels can be beneficial. These include lowering the total cholesterol level, lowering the total triglyceride level and increasing the ratio of high density lipoprotein (HDL) cholesterol to low density lipoprotein (LDL) cholesterol. This latter improvement is important because there is evidence that LDL is proatherogenic and HDL is antiatherogenic so that increasing HDL: LDL ratio provides a degree of protection from atherosclerosis and CAD.

Hyperlipidaemia can arise through a genetic disorder, as a result of other medical conditions or environmental influences, or a combination of these factors. Surprisingly, it has now been found that the administration of certain arylcyclobutylalkylamine compounds is effective in reducing lipid levels, particularly cholesterol and triglyceride levels.

Accordingly, the present invention provides a method for the prophylaxis and/or treatment of hyperlipidaemia, hypercholesterolaemia or hypertriglyceridaemia, comprising the administration, to a human in need thereof, of a therapeutically effective amount of a compound of formula I

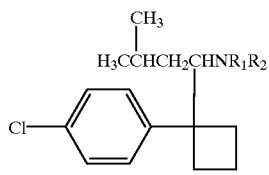

I including enantiomers and pharmaceutically acceptable salts thereof, in which $R_1$ and $R_2$ are independently H or methyl, in conjunction with a pharmaceutically acceptable diluent or carrier.

The method may also be used for the prophylaxis of atherosclerosis, coronary heart disease and/or coronary artery disease in humans at increased risk of developing these conditions.

The preparation and use of compounds of formula 1, such as N,N-dimethyl-1-[1-(4-chlorophenyl)cyclobutyl]-3-methylbutylamine (or N-(1-[1-(4-chlorophenyl)cyclobutyl]-3-methylbutyl)-N,N-dimethylamine) and salts thereof, in the treatment of depression is described in British Patent Specification 2098602. The use of compounds of formula I such as N,N-dimethyl-1-[1-(4-chlorophenyl)cyclobutyl]-3-methylbutylamine and salts thereof in the treatment of Parkinson's disease is described in European Patent Number 282206. The use of N,N-dimethyl-1-[1-(4-chlorophenyl)cyclobutyl]-3-methylbutylamine and salts thereof in the treatment of cerebral function disorders is described in U.S. Pat. No. 4,939,175. The use of N,N-dimethyl-1-[1-(4-chlorophenyl)cyclobutyl]-3-methylbutylamine hydrochloride in the treatment of obesity is described in European Patent Number 397831. A particularly preferred form of this compound is N,N-dimethyl-1-[1-(4-chlorophenyl)cyclobutyl]-3-methylbutylamine hydrochloride monohydrate (sibutramine hydrochloride monohydrate) which is described in European Patent Number 230742. The use of N,N-dimethyl-1-[1-(4-chlorophenyl)cyclobutyl]-3-methylbutylamine and salts thereof for improving the glucose tolerance of humans having Impaired Glucose Tolerance or Non-Insulin Dependent Diabetes Mellitus is described in published PCT application WO95120949.

It may be appreciated by those skilled in the art that compounds of formula I may exist as salts with pharmaceutically acceptable acids. Examples of such salts include hydrochlorides, hydrobromides, sulphates, methanesulphonates, nitrates, maleates, acetates, citrates, fumarates, tartrates [eg (+)-tartrates, (−)-tartrates or mixtures thereof including racemic mixtures], succinates, benzoates and salts with amino acids such as glutamic acid. Compounds of formula I and their salts may exist in the form of solvates (for example hydrates).

It will be appreciated by those skilled in the art that compounds of formula I contain a chiral centre. When a compound of formula I contains a single chiral centre it may exist in two enantiomeric forms. The present invention includes the use of the individual enantiomers and mixtures of the enantiomers. The enantiomers may be resolved by methods known to those skilled in the art, for example by formation of diastereoisomeric salts or complexes which may be separated, for example, by crystallisation; via formation of diastereoisomeric derivatives which may be separated, for example, by crystallisation, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesised by asymmetric synthesis using optically active reagents, substrates, catalysts or solvents, or by converting one enantiomer to the other by asymmetric transformation.

Specific compounds of formula I are N,N-dimethyl-1-[1-(4-chlorophenyl)cyclobutyl]-3-methylbutylamine, N-(1-[1-(4-chlorophenyl)cyclobutyl]-3-methylbutyl)-N-methylamine, and 1-[1-(4-chlorophenyl)cyclobutyl]-3-methylbutylamine including racemates, individual enantiomers and mixtures thereof, and pharmaceutically acceptable salts thereof. A preferred compound of formula I is N,N-dimethyl-1-[1-(4-chlorophenyl)cyclobutyl]-3-methylbutylamine or a salt thereof, for example the hydrochloride salt. A preferred form of this hydrochloride is its monohydrate.

The compound of formula I may be administered in any of the known pharmaceutical dosage forms. The amount of the compound to be administered will depend on a number of factors including the age of the patient, the severity of the condition and the past medical history of the patient and always lies within the sound discretion of the administering physician but it is generally envisaged that the dosage of the compound to be administered will be in the range 0.1 to 50 mg preferably 1 to 30 mg per day given in one or more doses.

Oral dosage forms are the preferred compositions for use in the present invention and these are the known pharmaceutical forms for such administration, for example tablets, capsules, granules, syrups and aqueous or oil suspensions. The excipients used in the preparation of these compositions are the excipients known in the pharmacists art. Tablets may be prepared from a mixture of the active compound with fillers, for example calcium phosphate; disintegrating agents, for example maize starch; lubricating agents, for example magnesium stearate; binders, for example microcrystalline cellulose or polyvinylpyrrolidone and other optional ingredients known in the art to permit tableting the mixture by known methods. The tablets may, if desired, be coated using known methods and excipients which may include enteric coating using for example hydroxypropyimethylcellulose phthalate. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by known methods and, if desired, provided with enteric coatings in a known manner. The contents of the capsule may be formulated using known methods so as to give sustained release of the active compound. The tablets and capsules may conveniently each contain 1 to 50 mg of the active compound.

Other dosage forms for oral administration include, for example, aqueous suspensions containing the active compound in an aqueous medium in the presence of a non-toxic suspending agent such as sodium carboxy-methylcellulose, and oily suspensions containing a compound of the present invention in a suitable vegetable oil, for example arachis oil. The active compound may be formulated into granules with or without additional excipients. The granules may be ingested directly by the patient or they may be added to a suitable liquid carrier (for example, water) before ingestion. The granules may contain disintegrants, eg an effervescent couple formed from an acid and a carbonate or bicarbonate salt to facilitate dispersion in the liquid medium.

The therapeutically active compounds of formula I may be formulated into a composition which the patient retains in his mouth so that the active compound is administered through the mucosa of the mouth.

Dosage forms suitable for rectal administration are the known pharmaceutical forms for such administration, for example, suppositories with cocoa butter or polyethylene glycol bases.

Dosage forms suitable for parenteral administration are the known pharmaceutical forms for such administration, for example sterile suspensions or sterile solutions in a suitable solvent.

Dosage forms for topical administration may comprise a matrix in which the pharmacologically active compounds of the present invention are dispersed so that the compounds are held in contact with the skin in order to administer the compounds transdermally. A suitable transdermal composition may be prepared by mixing the pharmaceutically active compound with a topical vehicle, such as a mineral oil, petrolatum and/or a wax, e.g. paraffin wax or beeswax, together with a potential transdermal accelerant such as dimethyl sulphoxide or propylene glycol. Alternatively the active compounds may be dispersed in a pharmaceutically acceptable cream, gel or ointment base. The amount of active compound contained in a topical formulation should be such that a therapeutically effective amount of the compound is delivered during the period of time for which the topical formulation is intended to be on the skin.

The therapeutically active compound of formula I may be formulated into a composition which is dispersed as an aerosol into the patients oral or nasal cavity. Such aerosols may be administered from a pump pack or from a pressurised pack containing a volatile propellant.

The therapeutically active compounds of formula I used in the method of the present invention may also be administered by continuous infusion either from an external source, for example by intravenous infusion or from a source of the compound placed within the body. Internal sources include implanted reservoirs containing the compound to be infused which is continuously released for example by osmosis and implants which may be (a) liquid such as an oily suspension of the compound to be infused for example in the form of a very sparingly water-soluble derivative such as a dodecanoate salt or a lipophilic ester or (b) solid in the form of an implanted support, for example of a synthetic resin or waxy material, for the compound to be infused. The support may be a single body containing all the compound or a series of several bodies each containing part of the compound to be delivered. The amount of active compound present in an internal source should be such that a therapeutically effective amount of the compound is delivered over a long period of time.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The invention further provides the use of a compound of formula I

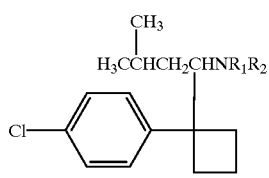

I including enantiomers and pharmaceutically acceptable salts thereof, in which $R_1$ and $R_2$ are independently H or methyl, in the manufacture of a medicament for the treatment and/or prophylaxis of hyperlipidaemia, hypercholesterolaemia or hypertriglyceridaemia In another aspect, the invention provides a pharmaceutical composition for the treatment and/or prophylaxis of hyperlipidaemia, hypercholesterolaemia or hypertriglyceridaemia, comprising a compound of formula I

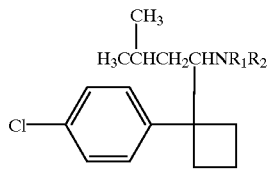

I including enantiomers and pharmaceutically acceptable salts thereof, in which $R_1$ and $R_2$ are independently H or methyl, in conjunction with a pharmaceutically acceptable diluent or carrier.

The present invention further provides a method of lowering lipid levels in the human body comprising the administration of a compound of formula I in conjunction with a pharmaceutically acceptable diluent or carrier to a human in need thereof. Preferably the lipid is a cholesterol or a triglyceride.

The present invention further provides a method of increasing the HDL cholesterol to LDL cholesterol ratio in the human body, comprising the administration of a compound of formula I in conjunction with a pharmaceutically acceptable diluent or carrier to a human in need thereof.

The present invention further provides the use of a compound of formula I in the manufacture of a medicament for lowering lipid levels in the human body. Preferably the lipid is a cholesterol or a triglyceride.

The present invention further provides the use of a compound of formula I in the manufacture of a medicament for the prophylaxis of atherosclerosis, coronary heart disease and/or coronary artery disease in humans at increased risk of developing these conditions.

The present invention further provides the use of a compound of formula I in the manufacture of a medicament for increasing the HDL cholesterol to LDL cholesterol ratio in the human body.

The present invention further provides a pharmaceutical composition for lowering lipid levels in the human body comprising a therapeutically effective amount of a compound of formula I in conjunction with a pharmaceutically acceptable diluent or carrier. Preferably the lipid is a cholesterol or a triglyceride.

The present invention further provides a pharmaceutical composition for the prophylaxis of atherosclerosis, coronary heart disease and/or coronary artery disease in humans at increased risk of developing these conditions, comprising a therapeutically effective amount of a compound of formula I in conjunction with a pharmaceutically acceptable diluent or carrier.

The present invention further provides a pharmaceutical composition for increasing the HDL cholesterol to LDL cholesterol ratio in the human body comprising a therapeutically effective amount of a compound of formula I in conjunction with a pharmaceutically acceptable diluent or carrier.

Compounds of formula I also have utility in the treatment of conditions associated with elevated Very Low Density Lipoprotein (VLDL), Intermediate Density Lipoprotein (IDL) or LDL levels, such as eruptive xanthomata, tuberous xanthomata, tendinous xanthomata and corneal arcus.

The efficacy of compounds of formula I in lowering lipid levels and increasing the HDL: LDL cholesterol ratio is illustrated by the following clinical trials. It will be appreciated by those skilled in the art that a 10 mg dose or 15 mg dose of sibutramine in the form of hydrochloride monohydrate is equivalent to 8.37 mg or 12.55 mg of sibutramine as free base respectively.

Trial 1

In a clinically supervised trial, 485 mild to moderately obese patients were randomised to receive placebo, sibutramine hydrochloride monohydrate (10 mg) or sibutramine hydrochloride monohydrate (15 mg) orally once daily for 12 months. Statistically significant reductions in triglyceride levels were observed in both sibutramine groups compared to placebo at month 6.

|                 | Percentage Change From Baseline | | |
|-----------------|---------|---------------------|---------------------|
| Assessment Time | Placebo | Sibutramine (10 mg) | Sibutramine (15 mg) |
| Month 6         | −3      | −18*                | −19**               |

*$p < 0.05$, **$p < 0.01$ compared to placebo.
'Sibutramine' means sibutramine hyrdochloride monohydrate Trial 2

In a further clinically supervised trial, 160 obese patients following a very low calorie diet were randomised to receive placebo or sibutramine hydrochloride monohydrate (10 mg) once daily for 12 months. Statistically significant (p<0.05) changes for a number of lipid variables were observed in favour of the sibutrarnine group, as illustrated in the following table:

| Variable | Assessment time | Median as a percentage of normal range | | p |
|---|---|---|---|---|
| | | Sibutramine (10 mg) | Placebo | |
| Apolipoprotein B/A1 ratio | Month 6 | −23% | −13% | 0.03 |
| | Month 12 | −10% | −3% | 0.02 |
| Apolipoprotein B | Month 6 | 7% | 15% | 0.049 |
| Triglycerides | Month 1 | 0% | 6% | 0.0014 |
| | Month 6 | −4% | 4% | 0.02 |
| | Endpoint | 0% | 4% | 0.04 |
| VLDL triglycerides | Month 1 | −4% | 3% | 0.045 |
| | Month 6 | −6% | 3% | 0.04 |
| HDL + LDL trigylcerides | Month 6 | −4% | 6% | 0.0105 |
| | Month 12 | 2% | 13% | 0.003 |
| | Endpoint | 1% | 9% | 0.008 |
| LDL–cholesterol | Month 6 | 20% | 32% | 0.02 |
| HDL–cholesterol | Month 12 | 34% | 18% | 0.003 |
| | Endpoint | 28% | 18% | 0.03 |
| Total cholesterol/HDL cholesterol ratio | Month 12 | −10% | −1% | 0.02 |
| LDL/HDL cholesterol ratio | Month 12 | −10% | 0% | 0.0099 |
| | Endpoint | −8% | 0% | 0.04 |

'Sibutramine' means sibutramine hydrochloride monohydrate

In obese patients with normal cholesterol levels sibutramine tended to reduce LDL cholesterol levels and increase HDL cholesterol levels. Significant increases in the ratios of HDL cholesterol to total cholesterol and HDL to LDL cholesterol were observed.

Further analysis of data

A meta-analysis of lipid profile based on weight lost, and a regression analysis comparing weight lost with changes in the co-morbid variable, was carried out on data from six clinical studies in obese patients in which fasting samples had been taken:

Summary of double-blind, placebo-controlled sibutramine hydrochloride monohydrate studies with fasting data

| Study | Co-morbid condition | Duration (weeks) | No. of patients included in meta-analysis | | | |
|---|---|---|---|---|---|---|
| | | | Placebo | 10 mg | 15 mg | 1–30 mg |
| 1 | | 24 | 102 | 116 | 114 | 694 |
| 2 | | 52 | 78 | 81 | — | 81 |
| 3 | Metabolic syndrome | 12 | 76 | 74 | — | 74 |
| 4 | Dyslipidaemia | 16 | 90 | 87 | — | 87 |
| 5 | Diabetes | 12 | 41 | — | 45 | 45 |
| 6 | Pre-diabetes | 24 | 58 | — | 50 | 50 |
| Total no. of patients[a]: | | | 445 | 358 | 209 | 1031 |

[a]Corresponding numbers of patients may be less for a given variable due to missing values.

Each meta-analysis was performed parametrically on the percentage change for lipids from baseline to endpoint (LOCF).

Data for all sibutramine hydrochloride monohydrate doses (1–30 mg) combined, sibutramine hydrochloride monohydrate 10 mg and 15 mg compared with placebo, categorised by all patients and those losing $\geq 25\%$ and $\geq 10\%$, is presented. The changes in risk for the sibutramine hydrochloride monohydrate patients who lost weight, ie with pharmacological intervention, were tested against the all patient placebo group, ie non-pharmacological intervention, using the same meta-analysis techniques.

Summary of mean percentage chance from baseline to endpoint for lipid variables in the meta-analysis of six studies with fasting lipids (LOFC analysis)

| Wt loss category | Mean wt change[a](kg) | Triglycerides | Cholesterol | | |
|---|---|---|---|---|---|
| | | | Total | LDL | HDL |
| Placebo | −2.1 | +2.4 (445) | +2.8 (445) | +5.0 (439) | +4.0 (443) |
| $\geq 5\%$ wt loss | −8.5 | −12.4 (98) | −1.6 (98) | −2.4 (98) | +4.8 (98) |
| $\geq 10\%$ wt loss | −12.1 | −14.4 (32) | −0.9 (32) | −5.6 (32) | +4.6 (32) |
| Sib 1–30 mg | −5.5 | −6.7***(1030) | +0.6**(1031) | +1.1**(1017) | +8.6***(1028) |
| $\geq 5\%$ wt loss | −9.7 | −15.8***(524) | −2.1***(524) | −1.4**(522) | +8.2**(524) |
| $\geq 10\%$ wt loss | −13.2 | −20.5***(234) | −4.5***(234) | −5.0***(234) | +9.8***(234) |
| Sib 10 mg | −5.5 | −8.0 (357) | +2.3 (358) | +3.2*(351) | +10.2**(356) |
| $\geq 5\%$ wt loss | −9.5 | −16.2**(187) | 0.4**(187) | +2.0 (186) | +10.1*(187) |
| $\geq 10\%$ wt loss | −13.4 | −13.5**(76) | −0.9*(76) | 0.9 (76) | +11.4 (76) |

-continued

Summary of mean percentage change from baseline to endpoint for lipid variables in the meta-analysis of six studies with fasting lipids (LOFC analysis)

| Wt loss category | Mean wt change[a](kg) | Triglycerides | Cholesterol | | |
|---|---|---|---|---|---|
| | | | Total | LDL | HDL |
| Sib 15 mg | −5.7 | −8.2 (209) | −3.1**(209) | −2.4 (204) | +5.6** (207) |
| ≧5% wt loss | −9.5 | −14.0**(109) | −5.5*(109) | −4.4 (108) | +4.7 (108) |
| ≧10% wt loss | −12.7 | −22.2**(48) | −8.4** (48) | −7.5* (48) | +5.8 (48) |

'Sib' means sibutramine hydrochloride monohydrate
[a]: Based on patients with triglyceride (TG) and total cholesterol (CHOL) data
Baseline values:
Placebo (mmol/l): TG 1.7; CHOL 5.6; LDL 3.5; HDL 1.3
Sib 1–30 mg (mmol/l): TG 1.8; CHOL 5.6: LDL 3.6; HDL 1.3
Sib 10 mg (mmol/l): TG 1.7; CHOL 5.6; LDL 3.4; HDL 1.3
Sib 15 mg (mmol/l): TG 1.9; CHOL 5.7; LDL 3.8; HDL 1.2
* $p < 0.05$ vs. all placebo
** $p < 0.01$ vs all placebo
*** $p < 0.001$ vs. all placebo
() Number of patients.

In this meta-analysis, patients treated with sibutramine hydrochloride monohydrate demonstrated statistically significant and clinically beneficial effects for all variables compared to placebo. More substantial positive effects are evident in those patients who lost clinically significant amounts of weight ie ≧5% and ≧10% of their baseline body weight.

The above results support the utility of compounds of formula I in lowering lipid levels and increasing the HDL:LDL cholesterol ratio in the human body.

What is claimed is:

1. A method for the prophylaxis or treatment of hyperlipidaemia, hypercholesterolaemia or hypertriglyceridaemia, comprising the administration, to a human in need thereof, of a therapeutically effective amount of a compound of formula I

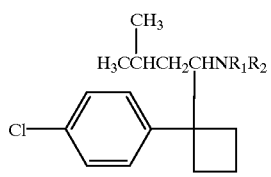

or an enantiomer or a pharmaceutically acceptable salt of the compound of formula I in which $R_1$ and $R_2$ of formula I are independently H or methyl, in conjunction with a pharmaceutically acceptable diluent or carrier.

2. The method of claim 1 wherein the compound of formula I is N,N-dimethyl-1-[1-(4-chlorophenyl) cyclobutyl]-3-methylbutylamine hydrochloride.

3. The method of claim 1 wherein the compound of formula I is N,N-dimethyl-1-[1-(4-chlorophenyl) cyclobutyl]-3-methylbutylamine hydrochloride in the form of its monohydrate.

4. A method of lowering lipid levels in the human body comprising the administration of a compound of formula 1, as defined in claim 1, to a human in need thereof in conjunction with a pharmaceutically acceptable diluent or carrier.

5. A method of prophylaxis of atherosclerosis, coronary heart disease and/or coronary artery disease in humans at increased risk of developing these conditions, comprising the administration of a compound of formula 1, as defined in claim 1, in conjunction with a pharmaceutically acceptable diluent or carrier to a human in need thereof.

6. A method of increasing the high density lipoprotein cholesterol to low density lipoprotein cholesterol ratio in the human body, comprising the administration of a compound of formula 1, as defined in claim 1, in conjunction with a pharmaceutically acceptable diluent or carrier to a human in need thereof.

7. A method for increasing HDL cholesterol levels in the human body comprising administering an effective amount of a compound as defined in claim 1 to a patient in need thereof.

* * * * *